United States Patent [19]

Thompson et al.

[11] 4,272,636

[45] Jun. 9, 1981

[54] CHLORINATED PHENOL MOLD RELEASE AGENT

[75] Inventors: Leonard R. Thompson; J. Kevin Kearney, both of Midland, Mich.

[73] Assignee: The Dow Chemical Company, Midland, Mich.

[21] Appl. No.: 106,991

[22] Filed: Dec. 26, 1979

[51] Int. Cl.$^3$ ............................................. C07C 39/36
[52] U.S. Cl. ..................................... 568/776; 568/755
[58] Field of Search ................................ 568/776, 755

[56] References Cited

U.S. PATENT DOCUMENTS

| | | | |
|---|---|---|---|
| 3,692,561 | 9/1972 | Hager et al. | 568/776 |
| 3,816,268 | 6/1974 | Watson | 568/755 |
| 3,839,469 | 10/1974 | Laufer | 568/779 |
| 3,852,160 | 12/1974 | Watson et al. | 568/755 |
| 3,852,161 | 12/1974 | Watson | 568/755 |
| 3,909,365 | 9/1975 | Christena | 568/755 |
| 4,016,047 | 4/1977 | Christena | 568/755 |
| 4,113,974 | 9/1978 | Mark et al. | 568/755 |
| 4,142,943 | 3/1979 | Kobel | 568/755 |

OTHER PUBLICATIONS

Kirk-Othmer "Encyclopedia of Chemical Tech." vol. 5, pp. 325-329.

*Primary Examiner*—Werren B. Lone
*Attorney, Agent, or Firm*—Charles J. Enright

[57] ABSTRACT

In an improved process for preparing chlorinated phenol by the reaction of molten phenol with chlorine in the presence of a Friedel-Crafts catalyst, the improvement comprises adding to the molten chlorinated phenol product, immediately on completion of the chlorination process, at least 0.5 weight percent of a glycol ether thereby inhibiting dioxin formation, inhibiting decomposition of the technical grade chlorinated phenol and most importantly, imparting mold release properties to the final product which is cast in corrosion-resistant molds, preferably stainless steel or plastic-lined steel molds.

8 Claims, No Drawings

CHLORINATED PHENOL MOLD RELEASE AGENT

BACKGROUND OF THE INVENTION

Chlorinated phenols exhibit outstanding germicidal and insecticidal properties and have demonstrated utility as flea repellants, fungicides, wood preservatives, mold inhibitors, etc. In general, biotoxic effectiveness increases with the degree of chlorine substitution. Technical grade chlorinated phenols have been found to decompose readily in the presence of metals, metal chlorides and heat to form large volumes of hydrogen chloride and tar. Product degradation is attributed to the presence of metal ions in storage and process vessels and small amounts of catalyst residue, i.e., aluminum and iron chlorides present in the technical grade chlorinated phenol product. Elevated temperatures are also known to accelerate the decomposition reactions.

In addition to decomposition difficulties, technical grade chlorinated phenols contain some impurities which give rise to objectionable color formation, typically a dark red or dark brown color. Other impurities include a family of high molecular weight compounds polychlorinated dibenzo-p-dioxins, known to have toxic properties. Other polychlorinated polynuclear impurities, the chlorinated phenoxyphenols, are a primary cause of blooming of the impure chlorinated phenol. Thus, high molecular weight impurities in the technical grade chlorinated phenols cause dark coloration, cause blooming and impart toxic properties in the form of dioxins.

Various processes of inhibiting decomposition of the crude chlorinated phenol during distillation are known. The distillation process has also, heretofore, facilitated the removal of dioxins formed. High boiling amines or alkanolamines have been disclosed as useful in stabilizing impure pentachlorophenol against decomposition during distillation (U.S. Pat. No. 3,816,268). Zinc dust or ethylene thiourea have been used to improve color and reduce the chlorodioxin content of impure pentachlorophenol during distillation (U.S. Pat. No. 3,909,365). Free-radical acting substances, e.g., phenols, hydroquinones, organic sulfur derivatives, organic phosphite, amine- and aldehyde-type compounds, have been used to improve color and reduce the chlorodioxin content of impure pentachlorophenol during distillation (U.S. Pat. No. 4,016,047). Polyhydroxy compounds, selected from the group consisting of sugars, polyhydric alcohols, polyglycols, and polyglycol ethers, have been incorporated into impure pentachlorophenol as decomposition inhibitors during distillation (U.S. Pat. No. 4,142,943). Salicylaldehyde and water and Reimer-Tiemann residues from the preparation of salicylaldehyde have also been disclosed as useful to remove impurities during the distillation of pentachlorophenol (U.S. Pat. No. 3,852,160 and 3,852,161).

The variety of materials offered for the purpose of producing chlorinated phenols which are desirable both from the aesthetic viewpoint and the environmental viewpoint is, to some extent, evidence that none is without disadvantage. Some of the materials identified by the prior art are very effective in inhibiting chlorinated phenol decomposition and/or preventing toxic by-product formation; however, neither of these desired results was possible without distillation. The underlying problems that have not been solved, by the prior art, are the formation of dioxins in the crude pentachlorophenol which made the distillation step necessary, and the lack of adequate mold-release properties in either technical grade or distilled product stored in corrosion-resistant vessels.

As an illustration, chlorinated phenols are conventionally prepared by the reaction of molten phenol with chlorine in the presence of a Friedel-Crafts catalyst such as aluminum chloride at temperatures which result in the production of a molten product. When the crude chlorinated phenol exits the reactor vessel in a molten state, further treatment, at temperatures above its freezing temperature, is required to prevent decomposition and toxic by-product formation. The treated chlorinated phenol product then proceeds to a storage vessel having a mold cavity where the mixture cools to a solid product. Heretofore, release of the solid product from the molds in which they are stored has presented severe difficulties. For example, the solid product adheres to the wall of the mold cavity and seriously complicates the subsequent removal and distribution of the chlorinated phenol product. It is desirable to efficiently remove the solid product from the mold cavity thereby providing a clean mold capable of accepting additional molten product. The utilization of an internal release agent in the treated chlorinated phenol product is also highly desirable and would avoid the obvious disadvantages of using an externally applied release agent to the mold cavity.

No prior art has been found which teaches the use of the compounds specified herein to impart mold-release properties to chlorinated phenols in addition to inhibiting dioxin formation and decomposition at high temperatures.

SUMMARY OF THE INVENTION

At least 0.5 weight percent of a glycol ether compounds, based on the total weight of molten chlorinated phenol product effectively imparts mold-release properties to the final product in addition to inhibiting dioxin formation and inhibiting decomposition of the technical grade chlorinated phenol prepared by chlorinating phenol in the presence of a Friedel-Crafts catalyst.

When molten chlorinated phenol containing a glycol ether compound is stored in corrosion-resistant molds, the product solidifies on cooling and yet remains easily extractable from the mold, preferably a stainless steel or plastic-lined steel mold.

DETAILED DESCRIPTION OF THE INVENTION

Although the process of the present invention may advantageously be performed on any crude or distilled chlorinated phenol, it has been found that the present process is particularly applicable to the treatment of pentachlorophenol to impart mold-release properties and significantly improve product quality with or without distillation, as desired.

In general, crude pentachlorophenol exits the reactor vessel in a molten state at temperatures above its freezing temperature, i.e., 185° C. If poured into a corrosion-resistant storage vessel prior to treatment with an inhibitor, the pentachlorophenol begins to decompose into hydrogen chloride (HCl) and tar. The early addition of a suitable amount of inhibitor retards decomposition of the pentachlorophenol and inhibits toxic dioxin formation when the crude molten product is being handled or stored in corrosion-resistant containers, at temperatures between 175° C. and 230° C. However, when the crude chlorinated phenol is allowed to cool to room temperature (23° C.) or below, it solidifies and has been found to adhere to the walls of the corrosion-resistant storage vessel. Dioxin formation occurs in any environment above 100° C. if the Friedel-Crafts catalyst residue remains active. Thus, in order to prepare a stabilized chlorinated phenol which is easily removed from a corrosion-resistant storage receptacle, it is advantageous to add a small amount of a mold-release agent, i.e., glycol ether compounds, directly to the crude chlorinated phenol in the molten state and before significant decomposition occurs. The addition of a glycol ether compound immediately after termination of chlorination, with agitation, gives the most beneficial results. By the process of this invention, decomposition of the crude chlorinated phenol is significantly retarded; toxic dioxin formation is reduced to acceptable parts per million levels, and the surprising and unexpected phenomenon that is the essence of this invention is the mold-release properties of the solid product. The chlorinated phenol containing a small amount of a glycol ether compound is easily released from the cavity of a corrosion-resistant storage receptacle.

The addition of at least 0.5 weight percent of a glycol ether compound, based on the total weight of the crude or distilled molten chlorinated phenol, effectively permits the release of stored, solidified product in contact with corrosion-resistant substrates, from the substrate using a minimal amount of release force. The glycol ether additive also inhibits dioxin formation and inhibits decomposition of molten, crude chlorinated phenols with or without distillation.

The glycol ether compounds used as internal release agents in chlorinated phenols, according to this invention, include mono-ethers of ethylene, diethylene and triethylene glycols; mono-methyl, -ethyl, -butyl, -isobutyl, and -phenyl ethers of glycols; and mono-ethers of propylene glycols.

The amount of glycol ether compound employed in the molten chlorinated phenol is not narrowly critical and can be varied considerably. The amount used depends largely upon the degree of release force desired. Very small amounts are effective in providing release properties. There can be used as little as 0.5 weight percent based on the total weight of a chlorinated phenol. Higher amounts up to 20 weight percent on the same weight basis can be used. A preferred range is from 1 weight percent to about 10 weight percent on the weight basis given above.

The addition of the glycol ether compound may be by any suitable means; however, it is preferred that the addition be accompanied by agitation, stirring or mixing so that a uniform mixture of the glycol ether and the chlorinated phenol results.

Typically, the glycol ether addition is performed at atmospheric pressure or above, for example 0 to 50 pounds per square inch gauge. The temperature for glycol ether addition can be from about 175° C. to about 230° C. The addition temperature is suitably above the freezing point of the chlorinated phenol and below the boiling point of the glycol ether compound additive. The early addition of the glycol ether compound will decrease the amount of tar in the feed, which as noted earlier begins to decompose soon after the chlorination reaction is terminated.

The choice of a storage vessel is not critical; however, in the production of large quantities (tons) of chlorinated phenol, it is recommended that the surface be able to withstand operating temperatures up to about 230° C. and be corrosion-resistant to maintain the chlorinated phenol in a nonroughened manner. By "corrosion-resistant" is meant sturdy and resistant to chemical changes (e.g., rusting, oxidizing processes) which cause a gradual wearing away or alteration of the surface. The walls of the container should be of a suitable thickness to prevent distortion of the molds. It is not required but preferred that the vessel surface contain a minimum amount of iron. The contact with iron causes the molten chlorinated phenol to darken; the degree of darkness depends on the length of time it is in contact with the iron.

Test Methods for Evaluating Mold-Release Properties

Prior to mixing the glycol ether additives with the molten chlorinated phenol, 125 ml cylindrical molds of stainless steel or polytetrafluoroethylene-lined steel, measuring 2½ inches in height and 2 inches in diameter, are cleaned with water and dried by wiping with a clean cheese cloth. A No. 10 wire hook is placed in each clean mold.

The quantity of glycol ether additive desired for mixing with the chlorinated phenol is added to an 8 oz. bottle containing the crude chlorinated phenol and heated to about 190° C. with occasional stirring until thoroughly blended. The molten glycol ether/chlorinated phenol mixture is then poured into the wire hook-containing cylindrical mold which is maintained at room temperature (~23° C.). After a 4-hour cooling period, the wire hook in each sample is independently attached to the load-measuring clamp of a Model J Tensile Tester. The amount of release force needed to pull the solidified chlorinated phenol from the cylindrical mold cavity is measured.

The Model J Tensile Tester is a brand of Scott Testers distributed by GCA/Precision Scientific, Chicago, Ill. and is more fully described in Bulletin 330/75, "Constant Rate-of-Traverse Tester, Model J", the contents of which are incorporated herein by reference. In Examples 1-7, a gear-driven recorder indicates the load in pounds of force (lbf) on a direct reading dial and a recording chart. The values recorded in Example 1 indicate that some adherence, although slight, has occurred. The foregoing procedure is used in developing release forces in Examples 1-7. In each example the chlorinated phenol is pentachlorophenol. The following examples illustrate the invention but are not to be taken as limiting its scope. In the examples, quantities of material are expressed in terms of parts by weight, unless otherwise specified.

EXAMPLES 1-7

In Table I below, Comparison A refers to a "Control" where no release agent was incorporated into the molten pentachlorophenol. Example 1 refers to an experiment where 1 weight percent of 2-(2-butoxyethoxy)-ethanol commercially available as DOWANOL ® DB (a trademark of the Dow Chemical Company) is incorporated. In Comparison B, materials used as dioxin and decomposition inhibitors are examined at the 1 weight percent level. Each sample, with and without an additive, is tested after the molten material had cooled to room temperature and solidified.

TABLE I

| | Mold-Release Tests | |
|---|---|---|
| Example/ Comparison No. | Additive* | Release Force in lb |
| 1 | DOWANOL DB | <1 |
| 2 | DOWANOL TBH | 2 |
| 3 | DOWANOL EB | <1 |
| 4 | DOWANOL DM | <1 |
| 5 | DOWANOL DE | 3 |
| 6 | DOWANOL PiB | <1 |
| 7 | DOWANOL PPh | <1 |
| A | None | 2 |
| B | PE-200 | 24 |

*The chemical composition of each additive is as follows: (DOWANOL ® is a trademark of The Dow Chemical Company)
DOWANOL DB - monobutyl ether of diethylene glycol
DOWANOL TBH - monobutyl ether of triethylene glycol and higher glycols
DOWANOL EB - monobutyl ether of ethylene glycol
DOWANOL DM - monomethyl ether of diethylene glycol
DOWANOL DE - monoethyl ether of diethylene glycol
DOWANOL PiB - monoisobutyl ether of propylene glycol
DOWANOL PPh - monophenyl ether of propylene glycol
PE-200 - polyethylene glycol (M.W. 200).

EXAMPLE 8

Measurement of Decomposition and Dioxin Formation

A 500 ml flask equipped with a thermometer, heat lamp and controller, 1"×1' glass tube condenser connected to a trap containing 100 cc of 1N sodium hydroxide is prepared to simulate high temperature storage conditions. To such prepared flask is added 266.4 grams of crude pentachlorophenol, containing residue from a Friedel-Crafts catalyst such as aluminum chloride, and 2.7 grams of DOWANOL DB additive. The mixture is heated, with stirring, and maintained at 190° C. for about 6½ hours. During this 6½-hour interval, nitrogen is slowly swept across the surface and bubbled into the sodium hydroxide trap. One-milliliter samples are withdrawn from the trap and titrated for HCl, one of the major decomposition products of pentachlorophenol. The titration is accomplished with 0.1N silver nitrate to give percent decomposition. The titration analysis reveals a small amount of HCl formation; <0.5 percent decomposition of pentachlorophenol under the conditions stated.

An aliquot of the above crude pentachlorophenol is also analyzed for chlorodioxin formation. Immediately following the chlorination of a molten phenol 1.25 grams of DOWANOL DB is added to 125 grams of crude pentachlorophenol, with agitation. Chlorodioxin formation is measured by liquid chromatography, at two intervals giving the following results.

| Time | Dioxins | |
|---|---|---|
| (Hrs.) | Hexachloro | Octachloro |
| 0 | <3 ppm | 594 ppm |
| 6½ | <3 ppm | 729 ppm |

The above data illustrate that glycol ether compounds of this invention not only make it possible to produce chlorinated phenol in a form that is easily extractable from corrosion-resistant storage vessels but also in a form which is very desirable from an environmental and industrial hygiene standpoint. The glycol ethers of this invention reduce the time and effort necessary to pull solidified chlorinated phenol blocks from the corrosion-resistant mold cavity and also inhibit product decomposition and toxic dioxin formation therein.

What is claimed is:

1. A process for imparting mold release properties to a chlorinated phenol prepared by chlorinating phenol in the presence of a Friedel-Crafts catalyst, comprising adding to a molten chlorinated phenol, immediately on completion of the chlorination process and without distillation at least 0.5 weight percent of a glycol mono ether compound selected from the group consisting of mono-methyl, mono-ethyl, mono-butyl, mono-isobutyl or mono-phenyl ethers of ethylene, diethylene, triethylene or propylene glycols.

2. A process for imparting mold release properties to a chlorinated phenol prepared by chlorinating phenol in the presence of a Friedel-Crafts catalyst, comprising adding to a molten distilled chlorinated phenol at least 0.5 weight percent of a glycol mono ether compound selected from the group consisting of mono-methyl, mono-ethyl, mono-butyl, mono-isobutyl or mono phenyl ethers of ethylene, diethylene, triethylene or propylene glycols.

3. The process improvement of claim 1 or 2 wherein the glycol mono compound ether is 2-(2-butoxyethoxy)ethanol.

4. The process improvement of claim 3 wherein said glycol mono ether is added in an amount of from about 0.5 to about 10 weight percent based on the total weight of the molten chlorinated phenol product.

5. The process improvement of claim 4 wherein the addition of said glycol mono ether compound is at temperatures between about 175° C. and about 230° C.

6. The process improvement of claim 1 or 2 wherein said glycol mono ether is triethylene glycol butyl ether containing highers.

7. The process improvement of claim 1 or 2 wherein the mixture of molten chlorinated phenol product and the glycol mono ether is continuously or substantially agitated to effect rapid, thorough blending of the components of said mixture.

8. The process improvement of claim 1 or 2 wherein the chlorinated phenol is pentachlorophenol.

* * * * *

UNITED STATES PATENT AND TRADEMARK OFFICE
CERTIFICATE OF CORRECTION

PATENT NO. : 4,272,636
DATED : June 9, 1981
INVENTOR(S) : Leonard R. Thompson and J. Kevin Kearney It is certified that error appears in the above—identified patent and that said Letters Patent is hereby corrected as shown below:

```
Column 1, line 24, "compounds" should read
    --compounds,--.

Column 2, line 19, "wall" should read --walls--.

Column 2, line 38, "compounds," should read --compound,--.

Column 4, line 51, the sentence that starts
    'The following examples. . .' should be a new
    paragraph.

Column 4, line 63, "the" should read "The".

Column 6, line 40, in Claim 3, "compound ether" should
    read --ether compound--.
```

Signed and Sealed this

Seventeenth Day of November 1981

[SEAL]

*Attest:*

GERALD J. MOSSINGHOFF

*Attesting Officer*  *Commissioner of Patents and Trademarks*